United States Patent [19]

Shih et al.

[11] Patent Number: 5,242,985
[45] Date of Patent: * Sep. 7, 1993

[54] AQUEOUS STABLE COMPLEX OF A STRONGLY SWELLABLE, MODERATELY CROSSLINKED POLYVINYLPYRROLIDONE AND IODINE

[75] Inventors: Jenn S. Shih, Paramus; John J. Merianos, Middletown, both of N.J.

[73] Assignee: ISP Investments Inc., Wilmington, Del.

[*] Notice: The portion of the term of this patent subsequent to Dec. 17, 2008 has been disclaimed.

[21] Appl. No.: 899,964

[22] Filed: Jun. 17, 1992

[51] Int. Cl.$^5$ .......................... C08F 8/22; C08F 26/10
[52] U.S. Cl. .................... 525/326.9; 525/356; 525/357; 526/258; 526/264; 524/80
[58] Field of Search .............. 524/80; 525/326.9, 356; 526/258

[56] References Cited

U.S. PATENT DOCUMENTS

| | | | |
|---|---|---|---|
| 3,898,326 | 8/1975 | Cantor et al. | 525/357 |
| 4,027,083 | 5/1977 | Herrle et al. | 525/326.9 |
| 4,320,114 | 3/1982 | Denzinger et al. | 525/358 |
| 4,345,049 | 8/1982 | Denzinger et al. | 525/326.9 |
| 4,758,674 | 7/1988 | Barabas | 525/326.9 |
| 4,851,543 | 7/1989 | Barabas | 525/326.9 |
| 4,954,351 | 9/1990 | Sackler et al. | 525/326.9 |
| 5,073,614 | 12/1991 | Shih et al. | 526/264 |

*Primary Examiner*—Paul R. Michl
*Assistant Examiner*—Olga Asinovsky
*Attorney, Agent, or Firm*—Walter Katz; Marilyn J. Maue; Joshua J. Ward

[57] ABSTRACT

What is described herein is a PVP-$I_2$ composition comprising strongly swellable, lightly crosslinked PVP complex to iodine, wherein said composition is capable of releasing free iodine slowly with time in the presence of water. Preferably the complex has about 10–15% by weight available iodine and about 4–8 weight % iodide, and is a free-flowing, fine, lightly yellow powder.

10 Claims, 1 Drawing Sheet

% Iodine Released vs. Time for Various PVP-$I_2$ Products in Water

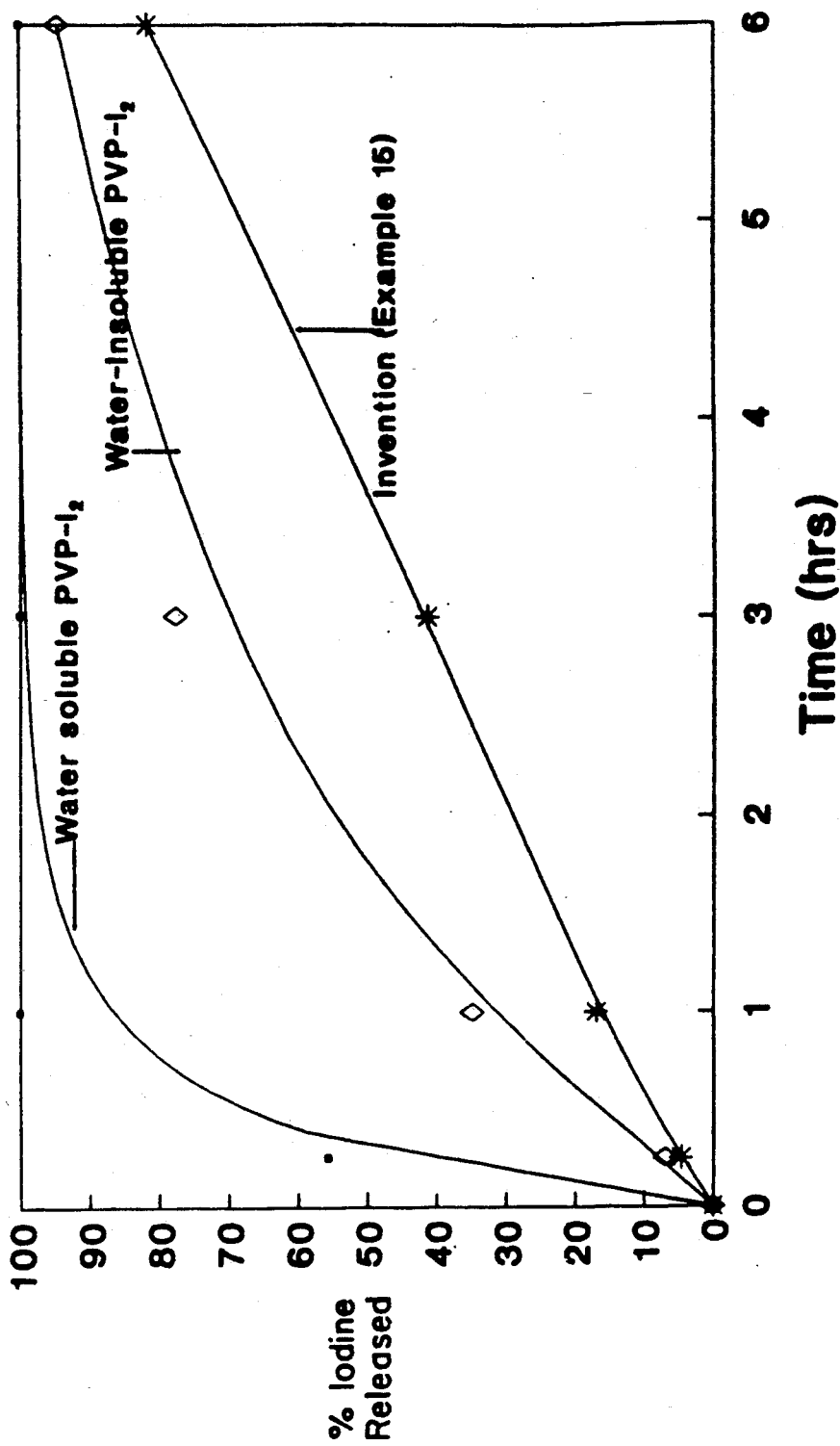

AQUEOUS STABLE COMPLEX OF A STRONGLY SWELLABLE, MODERATELY CROSSLINKED POLYVINYLPYRROLIDONE AND IODINE

BACKGROUND OF THE INVENTION

1. Field of the Invention

This invention relates to polyvinylpyrrolidone-iodine (PVP-$I_2$) complexes, and more particularly, to complexes of strongly swellable, lightly crosslinked PVP with iodine that exhibit antiseptic, broad-spectrum antimicrobial activity in a controlled and sustained manner.

2. Description of the Prior Art

Numerous potential pathogens may be present on the skin and exposed tissue. It is desirable for the growth of disease-producing microorganisms to be inhibited and preferaby for these microorganisms to be destroyed so as to control patient infection and encourage wound healing. As a result, the application to the skin or tissue of topical bactericidally active agents has become a standard part of the aseptic technique for wound care.

Iodine is an outstanding microbicide, with an extraordinary range of action. Part of its mode of action is that it is able to penetrate the cell walls of microorganisms rapidly, and block certain essential hydrogen-bonding in amino acids. Also, it has a powerful, oxidizing effect on S—H, group to form a —S—S— groups, which are essential factors in protein production. It is effective against a wide range of microorganisms, including bacteria, tubercle bacilli (Mycobacteria), fungi, protozoa, lipid and medium viruses, as well as non-lipid and small viruses. Iodine is designated as an intermediate germicide only because spores are not readily killed with weak concentrations. However, iodine has the greatest degerming efficiency compared to the other halogens, chlorine and bromine, since it is deactivated by proteins at least three times slower than chlorine and four times slower than bromine. Therefore, under normal conditions of use where there is the presence of large amounts of dissolved proteins as in blood, serum, or sputum, iodine would not be rendered ineffective. Iodine has the additional advantage that its disinfecting properties are independent of the pH value of its environment. Therefore, unlike chlorine, for example, iodine would not be rendered ineffective in an acid pH. It would likewise not be deactivated quickly in an alkaline pH.

Low concentrations of iodine react relatively slowly as compared with proteins in general and therefore it remains available to react with bacteria to which it generally has a greater affinity. It is in this way that iodine can exhibit its unique advantageous selectivity towards microorganisms while maintaining a very low level of cytotoxicity to the host cells. However, because of iodine's physical and inherent chemical properties, its use as an antiseptic, broad-spectrum antimicrobial has been limited because state of the art delivery methods allows for the liberation of too much free iodine which can be toxic to living cells.

Elemental iodine, in the form of Tincture of Iodine (alcoholic solution), is highly toxic if brought into contact with the body cavity. It causes swelling and bleeding of the mucous membranes. Iodine is therefore generally not impregnated into bandages because of the potential for this corrosive destruction of the skin. A 1% Tincture of Iodine solution can release in excess of 10,000 ppm of iodine into the surrounding tissue environment all at once, when only 0.5–2 ppm of iodine may be required to be antimicrobially effective. Consumption by an adult of 30 grams of Tincture of Iodine can be fatal. Also, elemental iodine is volatile having a high, intrinsic vapor pressure which causes, over time, a loss in germicidal potency. This occurs when the iodine content volatizes from coated surfaces or from antiseptic preparations, especially when exposed to the environment at elevated temperatures.

One example of an attempt to preserve or tame the outstanding antimicrobial activity of iodine, while simultaneously reducing its corrosive toxic and vapor pressure properties, is a two-part dressing, using an iodide salt in one component and an oxidizer in the other which react on moisture contact, liberating iodine, as described by Karns in U.S. Pat. No. 1,867,222. Another example is the use of water soluble complexes of polyvinylpyrrolidone and iodine (PVP/$I_2$) as disclosed by Lorenz in U.S. Pat. No. 4,128,633. The latter is illustrative of a complex of iodine and an organic carrier commonly known as an "iodophor". This complexing of iodine by PVP harnesses the iodine, thereby controlling its rate of release. However, both these aqueous solution complexes still have limited application in spite of their slower release properties, as their water miscibility with body fluids still causes excess delivery and quick dissipation of the released iodine, resulting in possible cytotoxicity and loss of long time effectiveness.

Iodophors are loose complexes of elemental iodine or triodide, solubilizers, and a polymeric carrier that serves, not only to increase the solubility of the iodine, but also to tame the iodine to provide a sustained release reservoir for the iodine. The carriers, heretofore, have been neutral, water soluble polymers, with mainly polyvinylpyrrolidones as the principal commercialized polymer. Polyether glycols, polyacrylic acids, polyamides, polyoxyalkylenes, starches and polyvinyl alcohol (PVA) also form iodophors. Carriers may also exhibit varying degrees of surface active properties that improve the penetration or wetting characteristics of the solution in use. Upon dilution, these iodophor complexes form micellar aggregates, which are dispersed, upon dilution, with water or bodily fluids, and the iodine linkage to the polymer is progressively weakened until the iodine can be regarded as free to generate antimicrobial concentrations. These iodine complexes in aqueous solution have the advantage over pure, elemental iodine solutions, in that because they are present in far less concentration they greatly reduce irritation to tissue, unpleasant odor, staining of tissue and corrosion of metal surfaces such as surgical instruments, but dissipate relatively quickly because of their miscibility and reaction with body fluids.

Generally, when such a complex is in equilibrium with the aqueous phase, and then diluted, the solution will have increased availability of free iodine within a given fixed volume. These iodophors, because of their water solubility, therefore tend to dissipate their antimicrobial action quickly, because as a solution, they are water miscible with fluids throughout the wound site, and react relatively quickly with serous fluids while reacting with the bacteria. The concentrations of iodine in water-based systems can be much higher than what is required for its antimicrobial intent, and iodine is dissipated by side reactions with body fluids, resulting in the iodine reservoir being prematurely used up and thus allowing recolonization of the wound site.

Compared to Tincture of Iodine, the improved release properties of PVP/I$_2$ iodophor have resulted in the greater use of iodine in preoperative skin preps, surgical scrubs, washes, douches, lotions and ointments. However, their limited iodine reserves and dilution factors have meant that such iodophors are effective for a given disinfecting purpose for a limited time only. Microorganisms that have survived the initial application, because of limited longevity of the antimicrobial agent, may act as a seed to cause the pathogen population to rise again to its initial level.

Most water miscible broad-spectrum antimicrobials exhibit this deficiency. Continuous application of the antimicrobial agent to the site is therefore required, to inhibit the increase in population. For example, sustained release can be provided, with prolonged antibacterial activity under a plastic, self-adhering surgical drape film. Rosso, in U.S. Pat. No. 4,323,557, describes a process for incorporating N-vinylpyrrolidone (NVP) in the polymeric backbone of a pressure-sensitive adhesive of which the pyrrolidone component serves to complex and slowly release the iodine. The iodophor-based adhesive film provides a sterile operative surface, and acts as a barrier to isolate the incision from contaminating skin flora. This product is for use as an incisible self-adhering drape and is not intended for wound healing dressings or wound packings.

A major disadvantage of PVP/I$_2$ complexes is that their safe and efficacious antimicrobial action is limited to use on skin or, in some cases, on intact mucosa. This is because their water solubility, as mentioned above, results in rapid and excess releases of free iodine when introduced into the wound site. Considering that as little as 0.2 ppm of iodine is sufficient to kill enteric bacteria (10 minutes at 25° C.), and under the same conditions, 3.5 ppm and 14.6 ppm of iodine, respectively, are sufficient to kill amoebic cysts and enteric viruses, PVP/I$_2$ complex solutions can instantaneously introduce thousands of excess parts of available iodine in one bolus (i.e., an uncontrolled burst of solution), dependent upon the site. Large concentrations of free iodine, as with borates, are cytotoxic and cytopathic to healthy tissue, and can have an adverse affect of reducing the body's natural defense mechanism against infection. A paper published in the British Journal of Surgery, 1986:73:95, stated "topical Povidone-Iodine not recommended for application on post appendectomy wounds". The paper was based on the results obtained from the appendicular fossa during the operations, and was predictive of the patients' likelihood to develop wound infection. In patients who had mixed aerobic and anaerobic culture results, 20% developed sepsis when PVP/I$_2$ was used, and 7% when systemic antibodies alone were used.

PVP/I$_2$ solutions are administered to open wound sites, as in burns, even though they are toxic, when stopping infection takes precedence over proper wound healing. Typical commercial antibacterials such as soap, Hexachlorophene, Hibiscrub, alcohol and Chlorhexidine are all water soluble and water miscible preparations which exhibit various efficacious antimicrobial properties on the skin, but all are relatively toxic upon contact with living cells.

Rosenblatt, in U.S. Pat. No. 5,071,648, polymerizes soluble PVA to form insoluble acetals in the form of foams, sheets or gels, and subsequently forms less soluble iodine complexes with these acetals with solutions of iodine, iodides, borates or their combinations. Such complexes of polyvinyl alcohol and iodine have a low solubility such that it releases iodine in a sustained and a controlled manner in an amount which will kill germ cells but not damage living tissue. An antimicrobial borate material may also be complexed with the polyvinyl alcohol. The complex may be with PVA or PVA acetal film, sponge, foam or gel and used as a wound dressing. The iodine is preferably complexed with hydroxylated polyvinyl acetal sponge and topically used. Additionally, the complex may be combined with a matrix, such as cloth or non-woven material.

Shih, in U.S. Pat. No. 5,073,614, described the preparation of strongly swellable, moderately or lightly crosslinked PVP having a predetermined aqueous swelling parameter and a defined viscosity which had effective thickener and gelling properties.

The reaction product of water soluble or water-insoluble PVP with elemental iodine, is marketed as a brown powder which contains about 11% of available iodine, i.e. active iodine, which can be titrated with sodium thiosulfate, and, in addition, contains about 5.5% of iodine in the form of iodide. At an iodine:iodide ratio of 2:1, the iodine bonding in the PVP-iodine complex is so strong that an iodine odor is no longer perceptible and a moist potassium iodide/starch paper introduced into the gas space above the PVP-iodine no longer acquires a color. In practice, the measure employed to assess whether the iodine is sufficiently firmly bonded is the partition coefficient of the iodine between an aqueous PVP-iodine solution and heptane, and this coefficient, as described, for example, in U.S. Pat. No. 3,028,300, should be about 200. Further it is necessary that in its formulations, in particular, in aqueous solution, the PVP-iodine complex should lose very little available iodine on storage, i.e. it should be very stable.

The prior art describes several methods for preparing such PVP-iodine complexes, including German Patent 1,037,075; U.S. Pat. Nos. 2,900,305; 4,402,937; 3,028,300; and 2,852,532; and German Published Application DAS 2,439,197.

In these references, very diverse measures have been described for the preparation of a stable PVP-iodine. For example, according to German Patent No. 1,037,075, the pulverulent PVP-iodine was subjected to a lengthy heat after-treatment at 90°–100° C.; while U.S. Pat. No. 2,900,305 proposed using a PVP having a defined moisture content for the preparation of a suitable PVP-iodine. U.S. Pat. No. 2,826,532 disclosed the addition of sodium bicarbonate; and U.S. Pat. No. 3,028,300 the addition of iodide in the form of hydrogen iodide or of an alkali metal iodide. U.S. Pat. No. 3,898,326 proposed the addition of hydrogen iodide or of an alkali metal iodide to an aqueous PVP solution, followed by reaction of the pulverulent PVP-iodide mixture, obtained from the solution after drying, with iodine. German Published Application DAS 2,439,197 stated that polyvinylpyrrolidone polymerized in an anhydrous organic solvent was particularly suitable for the preparation of a stable PVP-iodine.

The above prior art processes are also intended to permit economical preparation of a stable PVP-iodine. However, they also suffer from substantial disadvantages. According to the process described in German Patent 1,037,075, for example, heating for from 18 to 64 hours at 90°–100° C. to form the PVP-iodine complex was necessary to obtain a stable product having an iodine:iodide ratio of 2:1. The process described in U.S.

Pat. No. 2,900,305 entailed heating PVP and iodine for 22 hours at 90°-100° C.

According to U.S. Pat. No. 3,028,300, heating can be dispensed with if iodide in the form of an alkali metal iodide or hydriodic acid is added to the mixture of polyvinylpyrrolidone and iodine. This process, however, does not represent an optimum, since inhomogeneous mixtures are formed, in which the iodine is only weakly bonded, and, accordingly a strong smell of iodine is present. A related process without heat treatment was proposed in U.S. Pat. No. 3,898,326 wherein iodides, e.g. as HI or NaI, were added to an aqueous polyvinylpyrrolidone solution, drying, and the pulverulent polyvinylpyrrolidone/iodide mixture reacted with iodine. However, HI causes corrosion problems on drying, while NaI increase the alkali content above the stringent requirements of the drug laws. German Published Application DAS 2,439,197 suggested a heating time of 10 hours; however to achieve a partition coefficients of about 200 it was necessary to heat for at least 20 hours.

The heating times can be greatly reduced, as disclosed in German Published Application DAS 2,818,767, PVP is reacted with elementary iodine in the presence of formic or oxalic acids, or an ammonium salt or amide of carbonic acid, formic acid or oxalic acid.

U.S. Pat. No. 4,402,937 described the preparation of the product in water rather than the solid state. The process comprised reacting PVP with elemental iodine in the presence of formic acid, oxalic acid or an ammonium salt or amide of carbonic acid, formic acid or oxalic acid, in aqueous solution.

OBJECTS OF THE INVENTION

It is the central object of this invention to overcome the deficiencies of the foregoing antimicrobial solutions, by forming complexes which are less water miscible than those previously known, wherein iodine is complexed with polymeric, biocompatible materials which are less water soluble, to form antimicrobial iodophors that will release the iodine at a slow rate over an extended period of time.

It is a further object of this invention to form these less soluble complexes with vehicles such as films, gels and sponge foams, that exhibit a combination of superior physical properties such as high absorption of body fluids, strength, softness and hydrophilicity. Such vehicles, furthermore, should not leave residues or fibers behind, should be biocompatible, and should not, by themselves, support the growth of microorganisms. The iodine should not wash out of the complexes, but should remain active. Furthermore, these polymer systems should act as an iodine reservoir and hydrophilic bridge to the tissue for the transfer of controlled amounts of iodine, as in the transdermal drug delivery device, disclosed in U.S. Pat. No. 4,675,009.

It is another object of this invention to provide a stable aqueous complex of PVP-$I_2$ having an available iodine content of about 10-15% by weight iodine, the PVP being strongly swellable and moderately crosslinked, as defined by characteristic aqueous swelling and viscosity parameters, which is capable of releasing iodine slowly in the presence of water.

These and other objects and features of the invention will be made apparent from the following more particular description thereof.

SUMMARY OF THE INVENTION

What is described herein is a PVP-$I_2$ composition comprising strongly swellable, lightly crosslinked PVP complex to iodine, wherein said composition is capable of releasing free iodine slowly with time in the presence of water.

Preferably the complex has about 10-15% by weight available iodine and about 4-8 weight % iodide.

Accordingly, there is provided a free-flowing, fine lightly yellow powder of a substantially aqueous stable complex of a strongly swellable, moderately crosslinked PVP having an aqueous gel volume of about 15 to 150 ml/g of PVP and a Brookfield viscosity in 5% aqueous solution of at least about 10,000 cps, and $I_2$, the available iodine content being about 10-15% by weight of the complex, and wherein said composition is capable of releasing free iodine slowly in the presence of water.

IN THE DRAWINGS

The FIGURE is a graphical representation of % $I_2$ released with time for tablets of the complex of the invention in water compared with related complexes.

DETAILED DESCRIPTION OF THE INVENTION

U.S. Pat. No. 5,073,614 described strongly swellable, moderately crosslinked PVP polymers in the form of fine, white powders having (a) an aqueous gel volume of about 15 to 150 ml/g of polymer, (b) a Brookfield viscosity in 5% aqueous solution of at least about 10,000 cps, suitably, such polymers are prepared directly by precipitation polymerization of VP in the presence of a crosslinking agent in the amount of about 0.2 to about 1% by weight of VP, as described in U.S. Pat. No. 5,073,614.

In the preferred embodiment of this polymer (a) is 25 to 75 ml/g of polymer, (b) is at least 15,000 cps, and (c) is about 0.25 to 0.8%. In an optimum form of the invention, (a) is 30 to 60 ml/g, (b) is about 20,000 to 50,000 cps, and, the amount of crosslinker is about 0.35 to 0.6%.

Gel volume is a measure of the swelling property of the crosslinked polymer and is defined as the equilibrium aqueous swelling volume of polymer per unit weight, and is expressed in the units of ml/g. Gel volume is determined by first adding 1 g. of the polymer to a suitable graduated cylinder filled with water. This mixture then is shaken and allowed to stand at room temperature for 3 days. The volume of the gel which is produced in water is measured and taken as the gel volume. Similarly, the gel volume concept can be applied to non-aqueous systems.

Most preferably, the fine, white powder PVP polymers are prepared directly by a precipitation polymerization process in an organic solvent, such as an aliphatic hydrocarbon solvent, preferably cyclohexane or heptane, or an aromatic hydrocarbon, such as toluene, in the presence of about 0.2 to 1% by weight of VP of a crosslinking agent, preferably N,N'-divinylimidazolidone, triallyl-1,3,5-triazine-2,4,6(1H,3H,5H)-trione, and pentaerythritol triallyl ether at about 10 to 50% solids, preferably 15-30% solids, in the reaction mixture.

The invention will now be described in more detail by reference to the following examples.

PREPARATION OF STRONGLY SWELLABLE, MODERATELY CROSSLINKED PVP

EXAMPLE 1

A 2-liter, 4-necked reaction vessel was equipped with a condenser, a constant speed mechanical stirrer, set at 170 rpm with a torque indicator and an anchor agitator having an open radius of 4 and 5/6 inches, an adaptor for admitting nitrogen, and a thermocouple connected to a temperature controller. The vessel was charged with 1000 g. of cyclohexane and heated to 65° C. during 30 minutes while purging with nitrogen. The reactor then was held at 65° C. for an additional 30 minutes. Then 520 microliters of t-butylperoxy pivalate (Lupersol 11, 75% active) polymerization indicator was added. Thereafter a solution of 250 g. of vinylpyrrolidone and 1.25 g. of N,N'-divinylimidazolidone crosslinking agent was introduced into the charged reactor over a period of 4 hours while stirring the contents. The feeding rate was about 1.0 ml./min. Then the mixture was heated to 85° C. over a half-hour and held at that temperature for another half-hour. Then the mixture was transferred to a 2-liter high pressure reactor and 1.0 g. of 2,5-dimethyl-2,6-di-(t-butylperoxy)hexane (Lupersol 101, 90% active) was added. The reactor was sealed and heated to 130° C. for 8 hours, cooled to room temperature, and the mixture was dried in a rotary evaporator. The polymer product was oven dried at 100° C. and vacuum dried at 90° C. for 16 hours of each. A quantitative yield of a crosslinked PVP polymer containing about 0.5% crosslinking agent was obtained. The VP monomer content was 0.01%.

EXAMPLES 2-10

The procedure of Example 1 was followed using various amounts of different crosslinkers with the following results.

TABLE I

| Ex. No. | VP, Amount (g) | Cross-linker* | Crosslinker, Amount (g) | % Cross-linker | **Product Yield (%) |
|---|---|---|---|---|---|
| 2 | 250 | DI | 0.25 | 0.10 | 96.0 |
| 3 | 250 | DI | 0.625 | 0.25 | 100.0 |
| 4 | 250 | DI | 2.5 | 1.00 | 100.0 |
| 5 | 250 | PTE | 0.25 | 0.10 | 93.0 |
| 6 | 250 | PTE | 0.625 | 0.25 | 92.0 |
| 7 | 250 | PTE | 2.5 | 1.00 | 94.2 |
| 8 | 250 | MBA | 0.625 | 0.25 | 87.0 |
| 9 | 250 | MBA | 1.25 | 0.50 | 96.0 |
| 10 | 250 | MBA | 2.5 | 1.00 | 100.0 |

*DI = divinylimidazolidone,
PTE = pentaerythritol triallyl ether and
MBA = methylene bisacrylamide
**based upon VP used, by weight

EXAMPLES 11-12

The procedure of Example 1 was followed using heptane as solvent in place of cyclohexane. The feeding rate of the solution of vinylpyrrolidone in crosslinking agent was 0.50-0.55 ml./min. The results are shown in Table II below.

TABLE II

| Ex. No. | VP, Amount (g) | Cross-linker | Amount (g) | % Cross-linker | Product Yield % |
|---|---|---|---|---|---|
| 11 | 200 | DI | 1.0 | 0.50 | 95.6 |
| 12 | 250 | PTE | 1.25 | 0.50 | 91.5 |

DI - Divinylimidazolidone
PTE - Pentaerythritol triallylether

EXAMPLE 13

The reactor of Example 1 was provided with the anchor agitator positioned in the middle of the reactor and extended to within 2 inches of the bottom of the reactor. Two dip tubes were connected to two metering pumps. The thus-equipped reactor then was charged with the solvent which filled the reactor to about 4 inches above the bottom of the dip tubes. In this procedure, the solution of VP and crosslinking agent was admitted into the reactor through the dip tubes to a position below the surface of the solvent. The effect of such subsurface feeding of monomer-crosslinker solution was to reduce build-up of viscosity of the polymer product during the polymerization, resulting in a smoother course for the process, particularly with respect to effective stirring of the reaction mixture.

PROPERTIES OF PVP POLYMER OF EXAMPLES 1-13

EXAMPLE 14

The strongly swellable, moderately crosslinked PVP polymer powders of Examples 1-13 are characterized by its unique gel volume and viscosity, which properties enable the polymer to thicken aqueous and non-aqueous solutions effectively.

The viscosity of the polymer is defined by its Brookfield viscosity in cps, which is determined upon a 5% aqueous solution of the polymer at 25° C. by a standard analytical procedure using Model LTV and Spindle No. 4.

For maximum utility, it is desirable that the hydrated polymer exhibit a high gel volume and a high viscosity. With increasing cross inking density in the polymer, the gel volume decreases and viscosity increases and then decreases, passing through a maximum. In the crosslinked polymer system of this invention, an effective thickener product is provided by including crosslinker in the reaction mixture at a suitable concentration of about 0.2 to 1.0% by weight, based upon VP, preferably about 0.25 to 0.8%, and optimally, at about 0.35 to 0.6%. At this suitable amount of crosslinker loading, the crosslinked polymer product exhibits a gel volume of about 15 to 150 ml/g of polymer and a Brookfield viscosity of at least 10,000 cps. At the preferred crosslinker concentration, the gel volume is about 25 to 75 ml/g of polymer and its Brookfield viscosity is at least 15,000 cps. At the optimal amount crosslinker present in the reaction mixture, the polymer exhibits a gel volume of about 30 to 60 ml/g of polymer and a Brookfield viscosity of about 20,000 to 50,000 cps.

The viscosity of the crosslinked polymer of the invention is particularly substantially independent of extended storage time even at 50° C., and of pH, and is tolerant of monovalent and multivalent salts in solution.

As an added feature of the invention, the residual VP monomer content of the polymers obtained herein is less than about 0.1% by weight. In aqueous based processes, in contrast, the formation of a gel mass during polymerization may trap considerable amounts of VP monomer in the polymeric gel network.

PREPARATION OF STRONGLY SWELLABLE, LIGHTLY CROSSLINKED PVP-$I_2$

EXAMPLE 15

40 g. of the strongly swellable, lightly crosslinked PVP as prepared in Examples 1-14 was sprayed with 0.2 g. of isopropanol and then mixed with 8 g. of iodine at room temperature for 2 hours, then at 45° C. for 2 hours, and finally at 90° C. for 16 hours. The product was light yellow and free-flowing. Analysis: available iodine:10.72% (by wt.); iodide:4.75%; and moisture:3.49%.

EXAMPLE 16

The procedure of Example 15 was repeated using a mixture of 0.2 g. of isopropanol and 2 g. of water. The product was lightly yellow and free-flowing. Analysis: available iodine:11.36%; iodide:3.71% and moisture:4.07%.

EXAMPLE 17 COMPARATIVE AQUEOUS STABILITY PROPERTIES OF STRONGLY SWELLABLE, MODERATELY CROSSLINKED PVP-$I_2$

PRODUCTS OF INVENTION AND PVP-$I_2$ OF PRIOR ART

| Example | Characterization | Wt. Tablet (g) |
|---|---|---|
| 1 | Strongly Swellable, Moderately Crosslinked PVP-$I_2$ | 1.07 |
| U.S. Pat. No. 2,706,701 | Water Soluble PVP-$I_2$ | 0.73 |
| U.S. Ser. No. 773,165, Filed 10/8/91 | Crosslinked (Crospovidone) Water-Insoluble, PVP-$I_2$ | 0.53 |

The respective samples prepared above were tableted and added to 100 ml of water. Then 10 ml of the aqueous solution was removed periodically and analyzed for % $I_2$ released with time. The results are illustrated graphically in the FIGURE which demonstrate the particular aqueous stability of the products of the invention as compared complexes made with water soluble or crosslinked (water-insoluble) PVP. The gel products of the invention in 1-15% concentration, preferably about 4-8% by weight, also exhibit slow release of $I_2$ with time as compared to a more rapid release initially by the prior art complexes. As gel compositions, the invention complexes herein exhibit excellent thickening properties in both aqueous, organic and aqueous-organic solutions, such as alcohol, which can be utilized in cosmetic personal care, filter and pharmaceutical applications.

While the invention has been described with particular reference to certain embodiments thereof, it will be understood that changes and modifications may be made which are within the skill of the art. Accordingly, it is intended to be bound only by the following claims, in which:

What is claimed is:

1. A lightly colored, free-flowing, fine powder of a substantially aqueous stable complex of a strongly swellable, moderately crosslinked polyvinylpyrrolidone having an aqueous gel volume of about 15 to 150 ml/g of PVP and a Brookfield viscosity in 5% aqueous solution of at least about 10,000 cps, and $I_2$, wherein said complex has about 10-15% by weight available iodine and about 4-8 weight % iodide, which is capable of releasing iodine substantially uniformly over a 6 hour period in the presence of water.

2. A complex according to claim 1 wherein said polyvinylpyrrolidone is prepared by precipitation polymerization of vinylpyrrolidone in an organic solvent in the presence of about 0.2 to 1% by weight of a crosslinking agent, and a free radical polymerization initiator.

3. A complex according to claim 1 wherein said aqueous gel volume is about 25 to 75 ml/g. of polyvinylpyrrolidone, and said Brookfield viscosity is at least about 15,000 cps.

4. A complex according to claim 2 wherein said amount of crosslinking agent is about 0.35 to 0.6%.

5. A composition comprising about 1 to 30% by weight of the complex of claim 3 in a solvent.

6. A composition according to claim 5 comprising about 5 to 15% by weight of said complex.

7. A gel composition comprising the complex of claim 1 in an aqueous, organic or aqueous-organic solvent.

8. A gel composition according to claim 7 in which the complex is present in an amount of about 1-15% by weight of the composition.

9. A gel composition according to claim 7 wherein said complex is present in an amount of about 4-8%.

10. A gel composition according to claim 7 wherein said solvent is water or a water-alcohol mixture.

* * * * *